United States Patent [19]

Kelley et al.

[11] Patent Number: 5,118,493
[45] Date of Patent: Jun. 2, 1992

[54] COMPOSITION HAVING REDUCED NEPHROTOXOCITY COMPRISING A FATTY ACID CONTAINING COMPONENT AND CYCLOSPORINE

[75] Inventors: Vicki E. Kelley, Brookline, Mass.; William M. Bennett, Portland, Oreg.

[73] Assignees: Brigham and Women's Hospital; Oregon Health Sciences University

[21] Appl. No.: 639,757

[22] Filed: Jan. 11, 1991

Related U.S. Application Data

[63] Continuation of Ser. No. 318,591, filed as PCT/US87/01024, May 4, 1987, abandoned.

[51] Int. Cl.$^5$ .................. A61K 49/00; A61K 37/00; A61K 31/22; A61K 31/20
[52] U.S. Cl. ........................ 424/10; 514/11; 514/549; 514/560; 514/885
[58] Field of Search ............ 424/10; 514/11, 552, 514/560, 549, 885

[56] References Cited

U.S. PATENT DOCUMENTS 4.388.307  6/1983  Cavanak .................. 514/11

FOREIGN PATENT DOCUMENTS 0087865  9/1983  European Pat. Off. ........... 514/560

OTHER PUBLICATIONS

Kelley et al., "A Fish Oil Diet Rich in Eicosapentaenoic Acid Reduces Cyclooxygenase Metabolites, and Suppresses Lupus in MRL-lpr Mice", Journal of Immunology, vol. 134, No. 3, Mar. 1985.
Perico et al., "Functional Signifigance of Exaggerated Renal Thromboxane A$_2$ Synthesis Induced by Cyclosporin A", Instituted for Pharm. Research ©1986, 581-586.
Siess et al., "Platelet-Membrane Fatty Acids, Platelet Aggregation and Thromboxane Formation During Mackeral Diet", The Lancet, Mar. 1, 1980, 441-444.
Kelley et al., J. Immunol., 134(3):1914 (1985).
Chem. Abstr. vol. 99(3), 1983:21317t; Prickett et al.
Morley, J., Lymphokines, E. Pick. ed., Academic Press, NY, 4:377 (1981).
Lewis, G. P., Br. Med. Bull., 39:243 (1983).
Dunn, M. J., Renal Endocrinology, M. J. Dunn, ed., Williams & Wilkins, Baltimore, pp. 1-74 (1983).
Harrison's Principles of Internal Medicine, 10th ed., pp. 482-487 (1983).
Kawaguchi et al., Transplantation, 40(2):214 (1985).
Whisler et al., Transplantation, 38(4):377 (1984).
Foegh et al., Transplantation Proc., 16(6):1606 (1984).
Foegh et al., Transplantation Proc., 16(6):1603 (1984).
Khirabadi et al., Transplantation, 39(1):6 (1985).
Willis, A. L., Nutr. Rev., 39:289 (1981).
Dyerberg et al., The Lancet, 1:199 (1980).
Siess et al., The Lancet, 1:441 (1980).
Sanders et al., The Lancet, 1:1189 (1980).
Goodnight et al., Arteriosclerosis, 2:87 (1982).
Garton et al., Biochem. J., 50:517 (1952).
Bang et al., Acta Med. Scan., 192:85 (1972).
Bang et al., Acta Med. Scan., 200:69 (1976).
Dyerberg et al., The Lancet, 2:117 (1978).
Kelley et al., J. Immunol., 134(3):1914 (1985).
Kelley et al., J. Clin. Invest., 77:252 (1986).
Higa et al., Brazilian J. Med. Biol. Res., 18:355 (1981).
Beveridge, T., Prog. Allergy 38:269-292 (1986).
Endres et al., New. Eng. J. Med. 320(5):265-271 (1989).
Stoof, T. J. et al., J. of Internal Medicine 226:437-441 (1989).
van der Heide, J. J. et al., Transplantation 49:3:523-527 (1990).
Berthoux, F. et al., Nephrol. Dialy. Transpl. 5:745 (1991) (Abstract).
Brouwer, R. M. L. et al., Kidney International 40:342-348 (1991) (Abstract).

Primary Examiner—Frederick E. Waddell
Assistant Examiner—Raymond J. Henley, III
Attorney, Agent, or Firm—Sterne, Kessler, Goldstein & Fox

[57] ABSTRACT

Compositions comprising cyclosporine in combination with a vehicle comprising a fatty acid component comprising a fatty acid of the omega-3 or a pharmacologically acceptable salt thereof. Methods for mediating the nephrotoxic effect of cyclosporine and for reducing cyclosporine induced renal prostaglandins comprising administering said cyclosporine in combination with said fatty acid component or a pharmacologically acceptable salt thereof. Eicosapentaenoic acid and docosahexanoic acid are preferred omega-3 fatty acids of the present invention. The compositions and methods of the present invention are useful in clinical and preclinical therapeutic cyclosporine treatment of animals, including humans.

21 Claims, 1 Drawing Sheet

FIG. 1c ively in the treatment of various autoimmune diseases, including polymyositis, systemic lupus erythematosus, rheumatoid arthritis, and early insulin dependent diabetes see relevant chapters in: *Cyclosporine in Autoimmune Diseases*, ed. Schindler, R., Springer-Verlag, Berlin (1985), particularly von Graffenreid, B., et al., pp. 59–73).

COMPOSITION HAVING REDUCED NEPHROTOXOCITY COMPRISING A FATTY ACID CONTAINING COMPONENT AND CYCLOSPORINE

This application is a continuation of application Ser. No. 07/318,591, filed as PCT/US87/01024, May 4, 1987, now abandoned.

BACKGROUND OF THE INVENTION

1. Field of the Invention

This invention is directed to compositions comprising an effective amount of cyclosporine in combination with a fatty acid component comprising a fatty acid of the omega-3 family, and to a method for mediating the nephrotoxic effects of cyclosporine comprising administering said cyclosporine in combination with said fatty acid component.

2. Description of the Background Art

Cyclosporine is a cyclic, nonwater-soluble, highly nonpolar molecule composed of 11 amino acids. The compound is a promising immunosuppressive agent which is derived from soil fungus (Calne et al., *Transplant Proc.* 13:349–358 (1981); Ferguson et al., *Surgery* 92:175–182 (1982); Starzl et al., *Gynecol. Obstet.* 151:17–26 (1980)). The drug is now widely used for prolonging the function of various transplanted organs. Its immunosuppressive effects selectively inhibit T-cell function, allowing survival of allografts without myelosuppression, i.e., heart transplants, Myers et al., *N. Eng. J. Med.* 311:699 (1984).

In addition to its use in allograft recipients, recent clinical trials have been or are being undertaken to examine the efficacy of cyclosporine in the treatment of a wide variety of autoimmune diseases, including polymyositis, systemic lupus erythematosus, rheumatoid arthritis, and early insulin dependent diabetes see relevant chapters in: *Cyclosporine in Autoimmune Diseases*, ed. Schindler, R., Springer-Verlag, Berlin (1985), particularly von Graffenreid, B., et al., pp. 59–73).

Cyclosporine is a lipophilic molecule with a molecular weight of 1202 daltons. When the drug is dissolved in olive oil or a special solution prepared by the manufacturer, bioavailability and absorption are maximized. The drug readily binds to plasma proteins and has a terminal half-time of 24 hours. It is highly metabolized in the liver, with biliary excretion being the major route of elimination (Beveridge, T., *Cyclosporine A:, Proceedings of the International Symposium,* Cambridge, White D. J., ed., pages 35–44 (1982)). In addition to its immunosuppressive characteristics, the drug also has interesting anti-schistosome and anti-malarial activities (Kolata, *Science* (Washington, D.C.) 221:40–42 (1983); Sanches et al., *First Int'l. Montreux Conf. on Biol. Rhythms and Medications*, Montreux, Switzerland, March 26–30, 1984. Pergamon Press, Oxford (in press).

In spite of its great promise as an immunosuppressive, however, its use is somewhat limited, both by its association with infection and also because of hepatic and renal toxicities (Ryffel, OL 27–400: "Summary of Toxicity Data," Sandoz, Basel, Switzerland (1981)).

Clinical use of cyclosporine is associated with reversible, dose-related increases in blood urea nitrogen (BUN) and serum creatinine levels and depression of creatinine clearance. Some nephrotoxicity is reported to occur in almost 80% of renal transplant patients using cyclosporine (Kahan, B. D., *Dial. Transplant.* 12:620-30 (1983)). Often the urea nitrogen level is disproportionately increased relative to the serum creatinine level.

Frequent side effects of cyclosporine treatments in various autoimmune diseases include nephrotoxicity, hypertension, hyperkalemia, hyperuricemia, hepatoxicity, anemia, hypertrichosis, gingival hyperplasia, gastrointestinal intolerance, tremor, and paresthesia. von Graffenried, B., et al., in *Cyclosporine in Autoimmune Diseases.* R. Schindler, ed., Springer-Verlag, Berlin, pp. 59-73 (1985). Of these, the most commonly reported adverse effect is nephrotoxicity.

Bennett, W. M., et al., *Ann. Int. Med.* 99:851–854 (1983), have pointed out the substantial nephrotoxic potential accompanying cyclosporine therapy in patients receiving kidney, heart, bone marrow, and liver transplants. Acute cyclosporine nephrotoxicity is dose-dependent, correlated with cyclosporine levels in blood or plasma, Kahan, B. D., et al., *Transplantation* 34:36 (1982), and is reversible after dose reduction, Verani, R. R., et al., *Am. J. Kidney Dis.* 4:185 (1984), or after cessation of cyclosporine therapy, Chapman, J. F., et al., *Lancet I:*28 (1985).

Acute cyclosporine nephrotoxicity is morphologically correlated with tubular lesions characterized by inclusion bodies, isometric vacuolization and microcalcification, Mihatsch, M. J., et al., *Transplant Proc.* 15:2821 (1983). Various hypotheses have been proffered to explain the decline in glomerular filtration rate, as evident by the rapid increase of serum creatinine in cyclosporine-treated patients. These include stimulation of tubuloglomerular feedback, Gutshe, H. U., et al., Ninth Int. Congress of Nephrology, Los Angeles, June 1984, Abstract No. 475A (1984), and disturbance of the microcirculation through interaction of cyclosporine on local prostacyclin synthesis, Neild, G. H., et al., In B. D. Kahan, ed., *Cyclosporine,* Gruen & Stratton, Orlando, Florida, page 182 (1984).

By contrast to the mode of cyclosporine therapy used in transplant patients, patients with autoimmune diseases often receive lower initial dosages of cyclosporine for longer periods of time. von Graffenried et al., presented data extracted from case report forms of ongoing clinical studies of patients suffering from multiple sclerosis, rheumatoid arthritis, diabetes mellitus type I, uveitis posterior, primary biliary cirrhosis, endocrine ophthalmopathy and systemic lupus erythematosus. These data related to renal function in patients on continuous cyclosporine therapy for up to 24 months and to reversibility of nephrotoxic effects in patients after discontinuing cyclosporine treatment. They reported that cyclosporine induces an increase in serum creatinine within the first two weeks of therapy, and that the steepest decline in renal function occurs within the first three months of chronic treatment, with the mean reduction in creatinine clearance (CRCL) being 14% at month six. Only slight further CRCL impairment occurred after month six, and no relevant further deterioration was reported up to month 24 of cyclosporine therapy, although data for this duration of treatment were limited. The extent of nephrotoxicity was related to cyclosporine dosage and to cyclosporine levels, and may have been age-related. The authors concluded that these factors probably interacted in patients with rheumatoid arthritis, who also show above-average nephrotoxicity. Patients having below-average baseline renal function, however, showed only little and stable renal dysfunction despite average clinical dosage of cyclosporine. The authors observed that cyclosporine-induced renal dysfunction markedly improves after reduction of cyclosporine dose with subsequent lower creatinine levels, and is completely reversible within two months after stopping cyclosporine therapy. Similar reversibility of cyclosporine-induced nephrotoxicity has been reported in diabetes mellitus type I patients (Stiller, C. R., et al., *Science* 223:1362 (1984)) and in ocular inflammatory disorders of autoimmune origin (palestine, A. G., et al., *Am. J. Med.* 77:652 (1984)).

In contrast to the reversibility of renal dysfunction induced by chronic cyclosporine therapy in the treatment of autoimmune diseases, progressive and possibly irreversible cyclosporine-induced deterioration of renal function has been described in heart transplant patients (Myers, B. D., et al., *N. Eng. J. Med.* 311:699 (1984)). Possible irreversible histological findings in kidneys of transplant patients given cyclosporine therapy have also been published (Mihatsch, M. J., et al., *Transplant Proc.* 15:2821 (1983); Myers, B. D., et al., *N. Eng. J. Med.* 311:699 (1984)). And, in fact, von Graffenreid et al., supra, noted that, although the data from cyclosporine-treated patients suffering from autoimmune diseases seem to demonstrate full reversibility of cyclosporine-induced acute nephrotoxicity, a very slowly progressive chronic nephropathy could not be excluded, since the parameter used to assess renal function (serum creatinine) is not sensitive enough to detect early nephron loss, and because of the small amount of data for patient treatment beyond one year.

It will be apparent from the preceding discussion that deterioration of renal function is a major side effect which reduces the practical clinical therapeutic efficacy of cyclosporine treatment for transplant and non-transplant patients. The correlation of cyclosporine dose (and levels) with nephrotoxicity suggests that cyclosporine levels need to be maintained within a very narrow therapeutic range, i.e., low enough to minimize nephrotoxicity but high enough to accomplish immunosuppressive therapeutic objectives. For example, when cyclosporine is administered with the object of avoiding allograft rejection, a steady-state trough level of less than 200 ng/ml probably is not immunosuppressive enough to avoid rejection, whereas nephrotoxicity and other side effects occur more frequently at concentrations greater than 400 ng/ml. Such a narrow therapeutic window is difficult to maintain in clinical practice. Bennett, W. M., et al., *Ann. Int. Med.* 99:851–854 (1983). Furthermore, it has been suggested that any benefit derived from reduced rejection of renal allografts may be more than offset over the long term by chronic nephropathy induced by the cyclosporine therapy itself. Myers, B. D., et al., *N. Eng. J. Med.* 311:699–705 (1984). This same concern has been expressed where cyclosporine has been used to suppress the immune inflammation associated with autoimmune diseases, id., because of the risk of inducing severe chronic nephropathy. As a result of these concerns, Myers et al., supra, have also expressed the need for measures that would widen the margin of safety between the dose of cyclosporine required to achieve effective immunosuppression and the dose likely to cause renal damage.

While the mechanism of renal dysfunction is unclear, increased renal synthesis of thromboxane has been demonstrated during the progression of immune-mediated and non-immunologic induced models of renal injury. Lianos, E. A., et al., *J. Clin. Invest.* 72:1439–1448 (1983); Okegawa, T., et al., *J. Clin. Invest.* 71:8–90 (1983); Purkeroon, M. L., et al., *Kid. Inter. Abstr.* 25:251 (1984); Remuzzi, G., et al., *Kid. Inter. Abstr.* 25:217 (1984); Ichikawa, I., et al., *Kid. Inter. Abstr.* 25:231 (1984). Thromboxane, a prostanoid, is a metabolite of arachidonic acid derived from the cyclooxygenase pathway. The other prostanoids are the prostaglandins and prostacyclins. The prostanoids are potent mediators generated during immunologically related inflammatory events, and are capable of profoundly changing renal hemodynamics. Morley, J., in *Lymphokines*, E. Pick, ed. Academic Press, New York, 4:377–391 (1981); Lewis, G. P., *Br. Med. Bull.* 39:243–248 (1983); Dunn, M. J., in *Renal Prostaglandins* M. J. Dunn, ed., Williams & Wilkins, Baltimore, pp. 1–74 (1983). Prostanoids and eicosanoids, which are arachidonic acid metabolites, are synthesized by cells according to immediate need and are not stored in significant amounts for later release. *Harrison's Principles of Internal Medicine*, 10th ed., pp. 482–487 (1983).

Kawaguchi, A., et al., *Transplantation* 40(2):214–216 (1985), found that excretion of thromboxane B2, a urinary degradation product of thromboxane A2, is strongly correlated with serum cyclosporine levels in rats. The authors conclude that high cyclosporine doses are associated with increased synthesis of thromboxane B2 from renal or extrarenal sources. It is noted that, although clinical toxicity of cyclosporine bears a resemblance to the pathogenic properties of thromboxane A2, it is unclear whether the observed increase in thromboxane B2 synthesis is linked to cyclosporine-induced nephrotoxicity. Cyclosporine has also been reported to induce increased formation of prostaglandins of the E series (PGE) in cultured human monocytes. Whisler, R. L., et al., *Transplantation* 38:377–381 (1984). The authors note that this increased PGE formation requires cyclooxygenase activity, and suggest that this is mainly mediated through greater availability of endogenous arachidonic acid to the cyclooxygenase pathway.

Human kidney allograft rejection has been shown to be associated with an early increase in urinary excretion of immuno-reactive thromboxane B2 ($iTXB_2$) (Foegh, M. L., et al., *Transplantation Proc.* 16(6):1606–1608 (1984)) and has been suggested as an immunologic monitor in kidney transplant patients (Foegh, M. L., et al., *Transplantation proc.* 16(6):1603–1605 (1984)). Khiabadi, B. S., et al., *Transplantation* 39(1):6–8 (1985), report that increases in urinary $iTXB_2$ are associated with heterotropic cardiac allograft rejection in a rat model. The authors note that the precise relationship of urinary $iTXB_2$ through the rejection process is still conjectural and remains to be ascertained.

Active metabolites of arachidonic acid are formed by one of two synthetic pathways—the cyclooxygenase or the lipoxygenase system. The products of the cyclooxygenase pathway—the prostaglandin, prostacyclins, and thromboxanes—are collectively termed prostanoids. The term "eicosanoids" includes the products of the lipoxygenase pathway—5-hydroxyeicosatetraenoic acid and leucotrienes—and the prostanoids.

The initial synthetic step of both pathways involves cleavage of arachidonic acid from the phospholipid plasma membrane of cells. Free arachidonic acid can then be metabolized by the cyclooxygenase or lipoxygenase pathway. The first product of the cyclooxygenase pathway is the cyclic endoperoxide $PGG_2$, which is then converted to $PGH_2$. These are the key intermediates in the formation of the classical prostaglandins ($PGA_2$, $PGD_2$, $PGE_2$, and $PGF_2$-alpha), prostacyclin (PGI$_2$) and thromboxane A$_2$ (TXA$_2$). The first product of the lipoxygenase pathway is hydroperoxeicosatetraenoic acid (HPETE) which is an intermediate in the formation of 5-hydroxeicosatetraenoic acid (HETE) and the leukotrienes (LTA, LTB, LTC, and LTD). It is known that two fatty acids other than arachidonic acid—3,11,14-eicostriaenoic acid (dihomo-gamma-linolenic acid) and 5, 8, 11, 14, 17-eicosapentaenoic acid—can be converted to metabolites closely related to the prostanoids and eicosanoids. The products of these different fatty acid substrates are distinguished by their subscripts: the subscript 1 is given to products of dihomo-gamma-linolenic acid; the subscript 2 is given to arachidonic acid products; and products of 5,8,11,14,17-eicosapentaenoic acid are given the subscript 3. The subscripts additionally designate the number of double bonds between carbon atoms in the side chain of the products.

Arachidonic acid metabolites are rapidly catabolized in vivo. The E and F series prostaglandins are chemically stable, yet are almost completely degraded in a single pass through the liver and lungs. Thus, virtually all non-metabolized PGE measurable in urine derives from renal and seminal vesicle secretion, whereas PGE metabolites in urine represent PGE synthesis by other organs. PGI$_2$ and TXA$_2$ are chemically unstable and are also rapidly catabolized. PGI$_2$ is converted to 6-keto-PGF$_1$-alpha, and TXA$_2$ is converted to TXB$_2$. Both PGI$_2$ and TXA$_2$ are short-lived in vivo, and measurement of their inactive metabolites is the common method used to provide an index of their formation rates.

Arachidonic acid metabolites are postulated to play a role in the pathology of a number of diseases, including hypercalcemia of malignancy, bone resorption in rheumatoid arthritis and dental cysts, Bartter's syndrome, diabetes mellitus, essential hypertension, patent ductus arteriosus, peptic ulcer disease, dysmenorrhea, and asthma.

Several arguments support a relation between arachidonic acid metabolites and the inflammation response: endogenous prostaglandins are released in parallel by histamine and bradykinin; several arachidonic acid metabolites are known to cause vasodilation and hyperalgesia; prostaglandins are present in areas of inflammation, polymorphonuclear cells release PGE during phagocytosis and PGE is a chemotactic for leukocytes; increased vascular permeability, which results in local edema, is caused by some arachidonic acid metabolites; PGE-induced vasodilation is not abolished by atropine, propranolol, methylsergide, or antihistamines, which are known to antagonize other putative inflammatory response mediators, suggesting a direct inflammatory effect of PGE; arachidonic acid metabolites cause pain in animal models and hyperalgesia or increased sensitivity to pain in humans; PGE causes fever after injection into the cerebral ventricles or into the hypothalamus of experimental animals; and pyrogens cause increased concentrations of prostaglandins in cerebrospinal fluid, but prostaglandin synthesis inhibitors decrease fever and decrease release of prostaglandins into cerebrospinal fluid.

Metabolites of arachidonic acid also have a postulated role in the immune response. It is known that small amounts of PGE suppress stimulation of human lymphocytes by mitogens such as phytohemagglutinin, leading to the suggestion that these substances act as negative modulators of lymphocyte function, perhaps by a negative feedback control mechanism. Sensitivity of lymphocytes to the inhibiting effects of PGE$_2$ increases with age, and indomethacin augments lymphocyte responsiveness to mitogens to a greater degree in the elderly. Lymphocytes cultured from patients with Hodgkin's disease release more PGE$_2$ after the addition of phytohemagglutinin, and lymphocyte responsiveness is enhanced by indomethacin. When suppressor T cells are removed from the cultures, the amount of PGE$_2$ synthesized is diminished, and the responsiveness of the lymphocytes from the Hodgkin's patients and controls is no longer different. Depressed cellular immunity in patients with Hodgkin's disease may be the result of PGE inhibition of lymphocyte function. A general discussion of arachidonic acid metabolites relevant to medicine is presented in *Harrison's Principles of Internal Medicine*, 10th ed., pp. 482–487 (1983).

The obligatory precursor of arachidonic acid is linoleic acid (C18:2 omega-6). Linoleic acid is a polyunsaturated fatty acid of the omega-6 family. The omega number indicates the location of the first double bond counting from the methyl end of the fatty acid. The other two major unsaturated fatty acid families are the oleic acid (omega-9) family and the linoleic acid (omega-3) family. The three fatty acid families are not metabolically interconvertible. The major metabolite of oleic acid is eicostrienoic acid (C20:3 omega-9). The major omega-3 (linoeic) acid family metabolites are eicosapentaenoic acid (C20:5 omega-3) and docosahexaenoic acid (C22:6 omega-3). The principal foot sources of linoleic and linolenic acids are seeds and leaves. The major omega-3 fatty acids, eicosapentaenoic acid and docosahexaenoic acid, however, are synthesized by phytoplankton, which form the bottom of the marine food chain. As a result, fish, and especially fish oil, are enriched with omega-3-fatty acids, especially eicospentaenoic acid and docosahexaenoic acid. The omega-6 and omega-3 fatty acid families cannot be synthesized de novo by humans, and are regarded as essential fatty acids.

Other polyunsaturated fatty acids besides arachidonic acid may serve as substrates for prostaglandin synthesis. For example, dihomogamma-linolenic acid (DHLA) (C20:3 omega-6) acts as a substrate for prostaglands of the "1" series, such as the classical prostaglandin PGE$_1$. Willis, A. L., *Nutr. Rev.* 39:289–301 (1981). Eicosapentaenoic acid (C20:5 omega-3) is the substrate for prostaglandins of the "3" series and, under certain conditions, leads to the production of thromboxane A$_3$, PGA$_3$, and PGI$_3$. While feeding of linolenic acid (C18:3 omega-3) does not lead to significant increases of eicosapentanoic acid in adult human plasma (Dyerberg, J., et al., *Lancet* 1:199 (1980)), feeding of marine foods rich in eicosapentaenoic acid leads to rapid incorporation of this fatty acid into both platelet and endothelial cell membranes. See, e.g. Sless, W., et al., *Lancet* 1:441–441 (1980); Sanders, T. A. B., et al., *Lancet* 1:1189 (1980); and references cited in Goodnight, S. H., et al., *Arteriosclerosis* 2:87–113 (1982). In reviewing the effects of dietary polyunsaturated fatty acids of the various fatty acid families, Goodnight et al. concluded that feeding omega-3 fatty acid-rich fish oils to humans leads to a reproducible prolongation of the bleeding time, inhibition of platelet aggregation by ADP and collagen, as well as a decrease in platelet retention on glass beads. In some settings, the authors note, there may also be a reduction in platelet count. The authors conclude that ingestion of dietary fish oils containing the omega-3 fatty acid eicosapentaenoic acid may have profound effects on platelet or vessel composition and function. Cellular phospholipid concentrations of arachidonic acid are decreased, bleeding time prolonged, and various in vitro tests of platelet function are inhibited. One explanation offered by the authors for the platelet inhibition is the significant reduction in platelet thromboxane synthesis.

Ingestion of high levels of dietary fish oils may lead to undesirable side effects. For example, some fish oils contain high levels of cetoleic acid (C22:1 omega-11), an isomer of erucic acid (C22:1 omega-9). High levels of erucic acid are known to cause transient myocardial lipodosis and fibrosis in experimental animals. The Food and Agriculture Organization of the United Nations, Joint FAO/WHO Report, FAO Food & Nutrition Paper, No. 3, Rome, Italy (1977). Feeding high levels of fish oil also leads to the development of yellow fat disease in experimental animals. This disease is associated with vitamin E deficiency, which may be exacerbated by the highly unsaturated nature of omega-3 fatty acids. Garton, G. A., et al., *Biochem. J.* 50:517-524 (1952). Fish oil feeding affects platelet function, increasing bleeding times, and leads to thrombocytopenia in humans. All this suggests that is may be impractical or even unsafe for humans to ingest very high amounts of dietary fish oils, or to rely solely on fish oil as a lipid source. On the other hand, studies of human populations which historically consume high levels of omega-3 fatty acids, particularly the coastal Eskimos of Greenland, suggest that, aside from prolonged bleeding times and thrombocytopenia, there are no significant adverse effects of a high fish oil diet. Bang, H. O., et al., *Acta. Med. Scan.* 192:85-94 (1972); Bang, H. O., et al., *Acta. Med. Scan.* 200:69-73 (1976; Dyerberg, J., et al., *Lancet* 2:117-119 (1978).

Kelley, V. E., et al., *J. Immunol.* 134(3)1914-1919 (1985), supplemented the diet of MRL-1pr mice with fish oil as the exclusive lipid source and reported that this suppressed autoimmune lupus. The marine oil diet decreased lymphoid hyperplasia regulated by the 1pr gene, prevented increases in macrophage surface Ia expression, reduced formation of circulating retroviral gp70 immune complexes, delayed the onset of renal disease, and prolonged survival in these mice, as compared to mice given safflower oil as a lipid source. The authors postulate that the unique fatty acids, eicosapentaenoic acid or docohexaenoic acid, present in fish oils but not in vegetable or meat oils, are responsible for the observed reduction in autoimmunity, since both fatty acids are capable of modifying tissue and cellular cyclooxygenase metabolite levels. In addition to causing alterations in autoimmunity, the authors postulate that one or both of these unique fatty acids may decrease cyclooxygenase metabolites and protect the kidney from renal disease. Kelley, V. E., et al., *J. Clin. Invest.* 77:252 (1986). Using two different autoimmune mouse strains—MRL-1pr and NZBxNZW FI hybrid—having predictably progressive forms of lupus nephritis, which mimics human renal disease, the authors demonstrated an incremental increase in intrarenal $TXB_2$ synthesis as renal function deteriorated and renal pathologic events progressed, but no consistent increases in $PGE_2$ or 6-keto $PGF_1$ alpha, to other cyclooxygenase metabolites, were observed. Renal disease was prevented by either pharmacologic doses of $PGE_2$ or dietary supplementation with fish oil, in which case $TXB_2$ did not increase.

Prior to the present invention, then, a need has existed to reduce the substantial nephrotoxic effects of cyclosporine in order to allow the use of that drug in the clinical management of transplant and nontransplant patients. It has been noted that steady state trough levels of cyclosporine must be closely maintained to be sufficiently immunosuppressive to avoid transplant rejection and still avoid nephrotoxicity and other side effects of cyclosporine, and that this narrow therapeutic window is difficult to maintain in practice. A method that would allow clinicians to widen the margin of safety between the dose of cyclosporine required to achieve effective immunosuppression and the dose likely to cause renal damage would be of great therapeutic value in the treatment of transplant patients and patients suffering from immune diseases.

SUMMARY OF THE INVENTION

The present invention is directed to the discovery that fish oil, or certain active ingredients thereof, reduce the nephrotoxicity induced by administration of cyclosporine. The inventors have discovered that compositions, including emulsions of cyclosporine in fish oil or the active agents of fish oil, and therapeutic methods involving these compositions, allow administration of cyclosporine at higher effective clinical doses with significantly reduced nephrotoxicity. The use of fish oil or other oil predominantly consisting of omega-3 polyunsaturated fatty acids such as eicosapentanoic or docosahexanoic acids, as the vehicle for cyclosporine administration, increases the effective therapeutic dose of the cyclosporine therein and reduces renal dysfunction resulting from the cyclosporine. The compositions and methods of the present invention allow the use of higher steady-state cyclosporine doses for clinical treatment of transplant and nontransplant patients with reduced or eliminated nephrotoxic side effects. The utility of the present invention in the treatment of transplant patients and patients suffering from autoimmune diseases will be evident to one of skill in the relevant art.

DESCRIPTION OF THE PREFERRED EMBODIMENTS

Bu "cyclosporine" is meant a member of the group of biologically active metabolites produced by *Tolylocladium inflatum Gams* (formerly designated *Trichoerma polysporum Rifia*) and other fungi imperfecti. Some nine major and minor metabolites have been identified, designated cyclosporine A-I. Of these, the nonpolar cyclic oligopeptides, cyclosporine A, and cyclosporine C having immunosuppressant, antifungal, and antiphlogistic activity are preferred. Even more preferred is cyclosporine A.

By "therapeutically effective amount" is meant an amount of cyclosporine sufficient to produce a clinically beneficial result in the treatment of animals, preferably mammals, and more preferably humans. It will be recognized by one skilled in the clinical arts that the therapeutically effective amount of cyclosporine for a given clinical indication will necessarily vary according to the patient's needs and symptoms, and may be varied to suit these needs as a matter of course by one of skill. Thus, it is neither possible nor practically desirable to set arbitrary numerical limits on the therapeutically effective amount. A typical therapeutic amount of cyclosporine is in the range of 5-25 mg/kg/day.

The "fatty acid component of the present invention comprises a fatty acid containing an omega-3 fatty acid, said omega-3 fatty acid being either a synthetic product or derived from a natural product such as fish oil, seeds, leaves, phytoplankton, and the like. The "fatty acid component" may be either essentially pure omega-3 fatty acid or may contain the omega-3 fatty acid in an amount effective to reduce prostaglandin levels and/or mediate the nephrotoxic effects of cyclosporine.

A typical dosage of the active component is in the range of 1.25 to 6.25 mg/kg/day of the omega-3 fatty acid or an equivalent amount of fish oil. Further, 30-400 grams per day of fish will provide sufficient levels of the active component.

By "omega-3" is meant a polyunsaturated fatty acid having the first double bond three carbons from the methyl end of the fatty acid. This family includes linolenic acid (C18:3 omega-3), eicosapentaenoic acid (C20:5 omega-3), and docosahexanoic acid (C22:6 omega-3). Of these eicosapentaenoic and docosahexanoic acid, which are the predominant components of the marine oils, are preferred. Most preferred is eicosapentaenoic acid.

By "fish oil" is meant any oil derived from fish or from other forms of marine life, but preferably from fish. Preferred marine oils for the purposes of the present invention are salmon oil, cod liver oil, channel catfish oil, mackerel oil, and whale oil. Of these, cod liver oil is preferred, and mackerel oil is most preferred. Fish oil contains fatty acids of predominantly the omega-3 family.

By "pharmacologically acceptable" is meant a composition having sufficient purity, stability, and such other attributes as to make it acceptable for clinical or experimental administration to animals.

By "mediating" is meant having an effect on, preferably the effect of reduction. In the context of the present invention, mediating refers to the effect of reducing nephrotoxicity caused by cyclosporine.

By "administer" is meant to introduce to an animal, preferably a human. Modes of administration are well known in the medicinal arts, and include, but are not limited to, oral, rectal, vaginal, parenteral, intramuscular, intravenous, and intraperitoneal. The compositions and methods of the present invention may be administered by any method, as will be evident to those of skill in the art. Such methods include, but are not limited to, suspensions, solutions, tablets, and ointments.

Substitution of the fatty acid component of the present invention, preferably fish oil rich in fatty acids of the omega-3 family, and more preferably eicosapentaenoic acid, for the conventional olive oil vehicle used for cyclosporine administration markedly improves renal function and histology in cyclosporine therapy. Renal prostaglandins are also reduced. The result of the present invention is that clinical cyclosporine nephrotoxicity is reduced, allowing treatment with higher levels than heretofore possible, and producing greater clinical response at a given dose of cyclosporine. This beneficial result produced by the use of the compositions and methods of the present invention may be achieved without the need for high-fish oil diets, which may themselves result in undesirable side effects, where necessary.

Having now generally described the invention, understanding the same will be aided by reference to the following examples, which are not intended in any way to limit the scope of the claimed invention.

EXAMPLE I

Fish Oil as a Vehicle for Cyclosporine Modifies Experimental Nephrotoxicity and Reduces Renal Prostaglandins Groups of Male Fischer 344 rats (Simonsen Laboratories, Inc., Gilroy, California) weighing 250-300 grams were given 1 cc of fish oil (MaxEPA, RP., Scherer Corp., Troy, Michigan) or olive oil (The Napolean Company, Seattle, Washington) by once daily gavage. After 7 days (14 days in current study), cyclosporine (Sandoz, Inc., E. Hanover, New Jersey) was added to the fish oil and olive oil at 12.5 mg/cc and animals were treated daily with 50 mg/kg cyclosporine by gavage for 14 days. Control groups continued to receive fish oil or olive oil vehicles alone in equivalent doses. Animals were pair-fed standard rat chow to control for effects of cyclosporine-induced weight loss and allowed tap water adlibitium. Comparable-treated and control animals were designated for either renal prostanoid assays or glomerular filtration rate determination.

Renal Function and Pathology

Forty-eight hours prior to sacrifice, animals were singly housed in metabolic cages. Urines were collected for 24 hours prior to sacrifice and analyzed for concentrations of creatinine using a Cobas Bio-Centrifugation Analyzer (Roche Biomedical Instruments) and sodium by automatic fla photometer (Instrumentation Laboratories, Lexington, Massachusetts). At sacrifice, animals were anesthetized with ether and blood was drawn by direct cardiac puncture to determine concentrations of blood urea nitrogen using a Cobas Bio-Centrifugation Analyzer, creatinine, and sodium. Whole blood cyclosporine concentrations were determined by radioimmunoassay (Sandoz, Inc., E. Hanover, New Jersey). Both kidneys were removed and weighed. One kidney was sliced and formalin fixed and evaluated by light microscopy, by an observer who was unaware of treatment groups. Cortical tissue was obtained from the other kidney and analyzed for prostanoid levels by methods as described below.

Inulin Clearance

Rat were anesthetized with ketamine and given a primary dose of 0.25 uCi $^{14}$C-inulin in 6 ml 1% NaHCO$_3$ through femoral vein cannula, followed by a sustaining infusion of 2.5 uCi $^{14}$C-inulin in 10 ml 1% NaHCO$_3$ given at a rate of 52 ul/min. After a 30-minute equilibrium time, urine was collected over four periods of at least 20 minutes each via a cannula directly sutured into the bladder. Through a jugular vein catheter, 0.35 ml blood was drawn at the midpoint of each urine collection and replaced with equal volumes of 1% NaHCO$_3$. Inulin clearance values expressed as ml/min/100 g body weight represented the mean of the four clearance periods.

Extraction of Cyclooxygenase Metabolites

After removing the renal capsule, the kidney was bisected and the medulla and cortex separated by fine dissection. In addition, the lungs were removed from each mouse. Tissues were immediately moistened with Krebs-Ringer bicarbonate buffer (KRB) at pH 7.2 and 10-30 mg of tissue were uniformly minced with a razor blade and incubated in 2 ml KRB in a 25-ml flask on a shaker platform in a 5% $CO_2$ incubator at 37° C. for 15 or 30 min. All supernatants were immediately stored at −70° C. for $PGE_2$, $TXB_2$ (stable breakdown product of $TXA_2$), and 6-keto $F_{1a}$ from tissues, since prostanoids accumulate in the medium rather than in the tissues.

PGE, $TXB_2$, and 6-keto $PGF_{1a}$ assays

PHE, $TXB_2$, and 6-keto $PGF_{1a}$ contents of supernatant were determined by direct competitive binding radioimmunoassays. The anti-$PGE_2$ serum, provided by Dr. William Campbell, University of Texas Health Science Center at Dallas, Dallas, Texas, has a 14% cross-reactivity with $PGE_1$ but only 0.7% with $PGF_{2a}$. $TXB_2$ (the stable degradation product of $TXA_2$ antisera, a gift of Dr. P. V. Halushka (Medical College of South Carolina, Charleston, South Caroline) did not cross-react (0.04) with other arachidonic metabolites. $^3H$-$PGE_2$, $^3H$-$TXB_2$, and $^3H$-6-keto $PGF_{1a}$ were purchased from New England Nuclear (Boston, Massachusetts). Antiserum to the stable hydrolysis product of prostacyclin, 6-keto $PGF_{1a}$, was provided by Dr. Michael Dunn (Case Western Reserve Medical School, Cleveland, Ohio). All standards were provided by Dr. John Pike, Upjohn Co., Kalamazoo, Michigan. The expressed values for $PGE_2$, $TXB_2$, and 6-keto $PGF_{1a}$ represent the mean levels of duplicate determinations. Functionally equivalent anti-$PGE_2$ serum, $TXB_2$, and anti-sera to 6-keto $PGF_{1a}$ are commercially available as well.

Statistical Analysis

All data are expressed as the mean ± standard error of the mean. Comparisons made between the animals treated with cyclosporine in fish oil and those treated with cyclosporine in olive oil were made by Student's T test. The results are set forth in Table 1.

Results

Olive oil and fish oil alone produced no renal dysfunction although fish oil reduced prostanoids as expected. Whole blood cyclosporine A did not differ when either olive oil or fish oil was used as the vehicle. Cyclosporine A when administered with the fish oil vehicle could be qualitatively differentiated from cyclosporine A in olive oil by a marked reduction in proximal tubular vacuolization.

EXAMPLE II

Fish Oil as a Lipid Dietary Component Protects Against Cyclosporine-Induced Renal Dysfunction Male F 344 rats (Simonsen Laboratories, Inc., Gilroy, California) weighing 280-315 g were given 12.5 mg/kg/day Cyclosporine A (CSA) (Sandoz Pharmaceuticals, East Hanover, N.J.) by intraperitoneal injection for 2 weeks. Control rats received isovolumetric doses of the vehicle Cremophor EL (BASF, Parsil, N.J.). Pair feeding of experimental and control rats was started 4 weeks before commencing CSA or vehicle administration. The regimen for dietary fish oil has been described by Kelley et al., *J. Clin. Invest.* 77:252 (1986). All rats were pair fed a basic diet of 25% protein (casein), 49.5% carbohydrate (sucrose and dextrin), 20% lipid, and supplements (salt mix and L-cystine). The lipid dietary component was either omega-3 fatty acid-rich (35%) fish oil (Max-EPA, RP Scherer Inc., Clearwater, Fla.) or corn oil lacking these fatty acids.

Inulin Clearance

Inulin clearance was determined as described by Elzinga et al., *Transplan.* 43:271 (1987). Rats were anesthetized and given a dose of 0.25uCi $^{14}C$-inulin (New England Nuclear) in $NaHCO_3$ at a rate of 52 1/min. Following a 30 min equilibration, urine was collected at 20 minute intervals through a cannula sutured into the bladder. Blood (0.35 ml) was collected through a carotid catheter at the midpoint of each urine collection and quantitatively replaced with $NaHCO_3$. Serum and urine radioactivity was measured with a Beckman LS 100 liquid scintillation counter. Inulin clearance values, expressed as ml/min/100 g body weight, represent the mean of four clearance periods.

Renal Studies

Rats were anesthetized with ether and blood was drawn by direct cardiac puncture to determine serum creatinine (Cobas Autoanalyzer, Roche Diagnostics) as well as whole blood cyclosporine levels (Sandoz, Inc.). One kidney was excised for the assay of $TXB_2$, 6-keto $PGF_1$, and $PGE_2$. Cortical tissue (10-25 mg) was dissected, uniformly minced, and incubated in 2 ml Krebs Ringer bicarbonate buffer (pH 7.2 for 30 minutes at 37° C., and 5% $CO_2$. The supernatant was frozen until levels of the cyclooxygenase products were determined by radioimmunoassay. The remaining kidney from each animal was taken for light microscopic analysis and

TABLE I

Comparison of Renal Function and Renal Prostaglandins in Rats Receiving Cyclosporine A in Olive Oil or Fish Oil Vehicles

| | BUN (mg/dl) | Cr (mg/dl) | $C_{In}$ (ml/min 100 g) | $PGE_2$ | $TXB_2$ | $PGF_{1a}$ |
|---|---|---|---|---|---|---|
| FO + CSA | 21.8 ± 3.1 | .60 ± .02 | .41 ± .07* | 33 ± 7.7 | 15.3 ± 5.1 | 24.5 ± 7.3 |
| CO + CSA | 47.6 ± 19.6 | .91 ± .25 | .26 ± .09 | 73 ± 10.3 | 23.0 ± 5.4 | 41.9 ± 15.0 | n = 4 in each group.
*n = 6.
Values represent MEAN ± SEM.
Abbreviations:
FO Fish oil
OO Olive oil
CSA Cyclosporine A
BUN Blood urea nitrogen
CR Creatinine
In $^{14}C$ inulin clearance
$PGE_2$ Prostaglandin $E_2$
$TXB_2$ Thromboxane $B_2$
$PGF_{1a}$ 6-keto-$PGS_{1alpha}$ compared to controls by an observer unfamiliar with the treatment group. Kidney slices were fixed in formalin, embedded in paraffin and stained with hematoxylin and eosin.

Macrophage Stimulation

Macrophages were removed by peritoneal lavage with RPMI 1640 medium with L-glutamine containing penicillin (50 units/ml) streptomycin (50 g/ml) and sodium heparin (10 units/ml). The cells were diluted to $1 \times 10^6$/ml, plated on plastic petri dishes (4 ml/dish), and allowed to adhere for 1 hour at 37° C. in 5% $CO_2$. Nonadherent cells were removed by washing the plates x3 with RPMI. The remaining adherent cells are 95% macrophages. RPMI alone, or containing 50 g/ml *E. coli* endotoxin (List Biological Laboratories) or 1 M A23187 was added to the adherent cells. Following a 15 minute or 3 hour incubation, the supernatants were collected and frozen prior to radioimmunoassay.

TABLE II

| | INULIN CLEARANCE (Cin) AND BLOOD CsA LEVELS IN FISH OIL (FO) AND CORN OIL (CO) FED RATS | | |
|---|---|---|---|
| | | Blood CsA Levels (ng/ml) | |
| | Cin (ml/min/100 g) | 25/12.5 mg/kg⁻ | 12.5 mg/kg |
| CsA/FO | 0.33 ± 0.04* | 4108 ± 613 | 3218 ± 253* |
| CsA/CO | 0.01 ± 0.04 | 5716 ± 373 | 5404 ± 198 |

Data are expressed as mean ± SEM; n = 5 – 7/group. Cin was calculated from the $^{14}$C—inulin in the serum and urine at four 20 minute clearance periods. CsA levels were determined by radioimmunoassay.
⁻ Rats received 25 mg/kg for 1 week and the dose was reduced to 12.5 mg/kg for the second week due to toxicity.
*$p < 0.025$ compared to CsA/CO.

Radioimmunoassay $TxB_2$, 6-keto $PGF_1$ and $PGE_2$ content in supernatant was determined by direct competitive binding radioimmunoassay as described by Kelley et al., *J. Clin. Invest.* 77:252 (1986). Antiserum to $TxB_2$, used at a final dilution of 1:50,000, did not cross react (0.04%) with arachidonic acid or other metabolites. Anti-6-keto $PGF_1$ was used at a 1:15000 dilution. Anti-$PGE_2$ has a 14% cross-reactivity with $PGE_1$ and 2.7% with $PGF_2$, and was used at a final dilution of 1:6000. $^3H$-$TxB_2$, $^3H$-6-keto $PGF_1$, and $^3H$-$PGE_2$ were purchased from Amersham (Arlington Heights, Ill.). Expressed values for the metabolites represent mean levels of duplicate determinations.

Statistics

Data are expressed as the mean ± standard error of the mean. Statistical analysis of the data was performed using the Mann-Whitney U test. A value of $p\ 0.05$ was considered significant.

RESULTS

Renal Synthesis of $TxB_2$, $PGE_2$ and 6-keto $PGF_2$

As shown in Table II, chronic CSA administration to rats fed a control diet (CO) results in an altered pattern of cyclooxygenase metabolites produced by the renal cortex. CSA increased $TxB_2$ levels from 23.1±1.4 to 49.2±4.9 pg/mg (p 0.01, CO vs CSA/CO). In contrast, CSA treatment resulted in a reduction in $PGE_2$ (93.8±8.0 vs. 72.2±7.1 pg/mg, p 0.05), wile 6-keto $PGF_1$ levels remained unaffected by CSA treatment (19.5±1.0 vs. 20.3±2.6 pg/mg).

Rats fed a fish oil diet with or without CSA treatment exhibited reduced renal synthesis of the three cyclooxygenase products tested (Table III). The combined treatments (CSA/FO) resulted in still lower levels of $TxB_2$ compared to the FO alone group (10.3±1.0 vs. 17.0±1.3 pg/mg, p 0.01). The 6-keto $PGF_1$ levels, which were unaffected by CSA treatment in the control diet group, were further reduced by CSA in the fish oil diet group. (11.9±1.8 (FO) vs. 6.8±1.1 pg/mg (CSA/FO), p 0.05).

In renal medulla, CSA induced $TxB_2$ in rats on a CO diet (565.7±33 pg/mg tissue) as compared to these animals on FO diet (325.7±48 pg/mg tissue). These results suggest that the enhanced Tx synthesis is not unique to the renal cortex, but also occurs within the renal medulla.

Macrophage Stimulation Studies

Figure 1A:
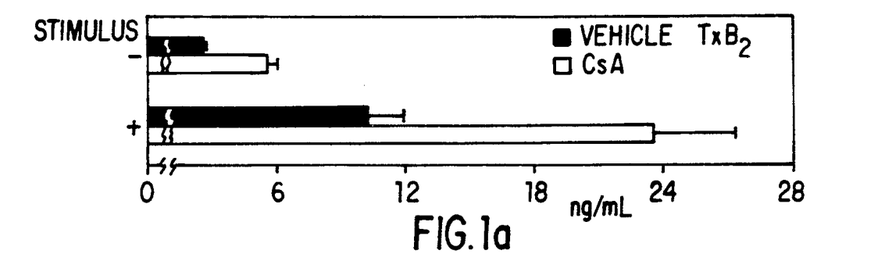
FIGS. 1a, 1b and 1c show the effect of cyclosporine A on A23187-stimulated macrophage cyclooxygenase products.
Figure 1B:
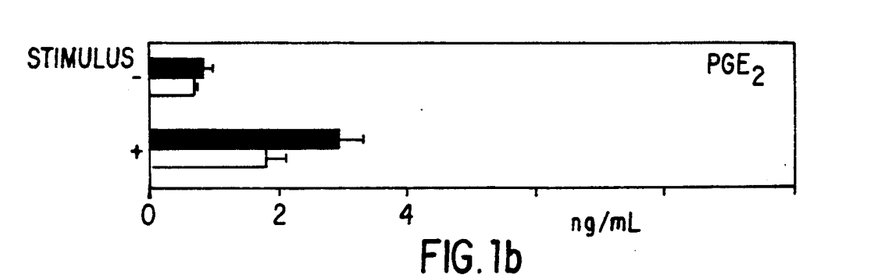
Figure 1C:
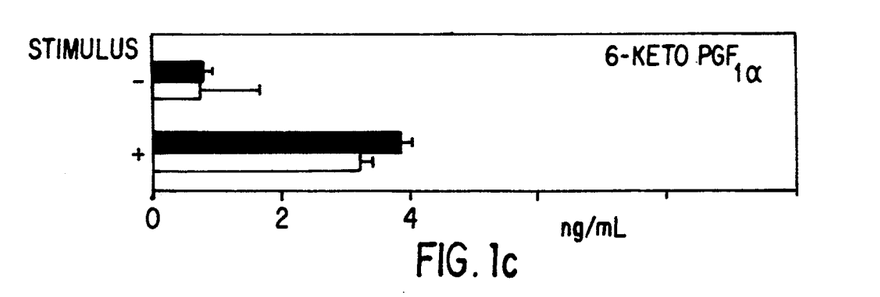

As shown in FIG. 1 peritoneal macrophages from CSA-treated rats exhibit increased basal (5.2±0.4 vs. 2.4±0.2 ng/ml, CSA vs. vehicle, p 0.01) and A23187-stimulated (21.9±3.5 vs. 9.6±1.5 ng/ml, p 0.01) TxB synthesis compared to Vehicle controls during a 15 minute incubation. In contrast, basal levels of $PGE_2$ and 6-keto $PGF_1$ produced by macrophages from CSA-treated rats were not different from vehicle-treated controls. In addition, A23187-stimulated $PGE_2$ and 6-keto $PGF_1$ synthesis is decreased (p 0.05, CSA vs. vehicle) as a result of CSA treatment.

Table III shows the effect of CSA treatment on LPS and A23187 stimulated cyclooxygenase products by macrophages during a 3 hour incubation. CSA treatment results in increased $TxB_2$ levels during stimulation with LPS (36.4±0.3 vs. 16.0±0.8 ng/ml, CSA vs. vehicle, p 0.02) or A23187 (34.0±2.4 vs. 13.6±1.1 ng/ml, p 0.02). Basal $TxB_2$ levels (10.7±0.2 ng/ml) were not different from vehicle controls (11.2±1.7 ng/ml). Basal level of $PGE_2$ were decreased in the CSA group (0.9±0.2 vs. 1.9±0.1 ng/ml, p 0.02), but LPS and A23187-stimulated $PGE_2$ production were not altered

TABLE III

| | CsA INDUCES $TxB_2$ IN THE RENAL CORTEX - FISH OIL | | |
|---|---|---|---|
| | $TxB_2$ | $PGE_2$ pg/mg | 6-Keto $PGF_{1\alpha}$ |
| CsA/CO | 49.2 ± 4.9 | 72.2 ± 7.1 | 20.3 ± 2.6 |
| CsA/FO | 10.3 ± 1.0 | 23.4 ± 2.7 | 6.8 ± 1.1 |
| CO | 23.1 ± 1.4 | 93.8 ± 8.0 | 19.5 ± 1.0 |
| FO | 17.0 ± 1.3 | 28.1 ± 5.0 | 11.9 ± 1.8 |

Data are expressed as x̄ ± SEM; n = 4-5/group. Renal cortex (10-25 mg) was minced and incubated at 37° C. in krebs Ringers bicarbonate buffer for 30 min. Levels of cyclooxygenase products released into the medium were measured by radioimmunoassay.

by CSA (Table IV). Similarly, basal levels of 6-keto PGF$_1$ were decreased (p 0.02) in the CSA treated group, while LPS and A23187-stimulated production was not different.

TABLE IV

IN VIVO EFFECTS OF CsA ON MACROPHAGE STIMULATION

| | TREATMENT | STIMULUS | ng/ml |
|---|---|---|---|
| A. TxB$_2$ | Vehicle | — | 11.2 ± 1.7 |
| | | LPS | 16.0 ± 0.8 |
| | | A23187 | 13.6 ± 1.1 |
| | CsA | — | 10.7 ± 0.2 |
| | | LPS | 36.4 ± 0.3* |
| | | A23187 | 34.0 ± 2.4* |
| B. PGE$_2$ | Vehicle | — | 1.9 ± 0.1 |
| | | LPS | 2.2 ± 0.1 |
| | | A23187 | 4.7 ± 0.3 |
| | CsA | — | 0.9 ± 0.2* |
| | | LPS | 2.7 ± 0.3 |
| | | A23187 | 3.1 ± 0.1 |
| C. 6-Keto PGF$_{1\alpha}$ | Vehicle | — | 2.9 ± 0.2 |
| | | LPS | 3.3 ± 2.4 |
| | | A23187 | 4.5 ± 0.2 |
| | CsA | — | 1.3 ± 0.04* |
| | | LPS | 3.2 ± 0.1 |
| | | A23187 | 4.1 ± 0.4 |

Peritoneal macrophages from CsA- and vehicle-treated rats were diluted to 1 × 10$^6$/ml and incubated in RPMI 1640 containing 50 mg/ml LPS or 1 mM A23187 for 3 hr at 37° C.
*p < 0.02 compared to vehicle group

Renal Function and Other Studies

Dietary FO protects against CSA-induced renal failure as indicated by increased (p 0.25) inulin clearance compared to the CO group (Table IV). Trough blood CSA levels (ng/ml) were determined following 2 different CSA does regimens. One group (25/12.5 mg/kg) was given 25 mg/kg CSA for the first week, and the dose was reduced to 12.5 mg/kg for the following 2 weeks. The large doses of CSA resulted in high levels of CSA in the blood of these rats. The second group tested was given 12.5 mg/kg for 2 weeks. As shown in Table IV, the blood CSA levels in the rats given 25/12.5 mg/kg were similar in the CSA/FO (4108±613 ng/ml) and CSA/CO (5716±373 ng/ml) groups. However, levels in the rats given doses of 12.5 mg/kg were not similar, which was unexpected. CSA concentrations were reduced in the CSA/FO group (3218±253 ng/ml) compared to the CSA/CO group (5404±198 ng/ml).

The effect of CSA as well as the FO diet on weight change during the treatment was determined. FO alone had no effect on weight change compared to CO alone (±24.8±2.2 g vs. +23.8±2.3 g, respectively). CSA treatment did result in weight loss and FO did not affect the amount lost [−5.2±2.7 g (CSA/FO) vs −3.8±7.7 g (CSA/CO)] due to effective pair feeding.

Histologic examination by light microscopy revealed morphologic changes within the proximal tubule in animals treated with CSA, including intracellular vacuoles similar to those previously described (The Canadian Multicentre Transplant Study Group, *N. Eng. J. Med.* 301:809 (1983)). The CSA/FO group showed a marked reduction in tubular vacuolization. No morphologic changes were observed in the groups treated with vehicle alone.

DISCUSSION

Chronic pretreatment of rats with CSA results in increased TxB$_2$ synthesis by the renal cortex and peritoneal macrophages, while 6-keto PGF$_1$ and PGE$_2$ synthesis is unaffected or decreased. In addition, dietary fish oil prevents the increase in TxA$_2$ and protects rats from CSA-induced nephrotoxicity. No adverse side effects of high dietary fish oil were observed.

Several investigators have reported that CSA stimulates synthesis of arachidonic acid metabolites. The instant results are in agreement with those of Perico et al., *Am. J. Physiol.* 251:F581 (1986) reporting increased urinary thromboxane levels in CSA-treated rats. However, Coffman et al., *Transplan.* 43:282 (1987) reported increased TxB$_2$, 6-keto PGF$_1$ and PGE$_2$ production in ex vivo perfused kidneys and increased urinary TxB$_2$ and 6-keto PGF$_1$ levels in rats pretreated with CSA. Whisler et al., *Transplan.* 38:377 (1984) examined the effect of incubation with CSA on human monocytes in vitro and found that CSA stimulated PGE$_2$ production in a dose-dependent manner. The discrepancies between these reports and the present studies are likely due to different experimental protocols (ex vivo perfusion vs. minced cortex) and method of CSA exposure (in vitro vs. in vivo).

The decrease in renal dysfunction in rats receiving CSA and FO was not caused by a change in bioavailability of CSA. Blood levels of CSA in FO or olive oil were similar despite modification of nephrotoxicity by dietary FO. Large doses of CSA given to rats on a FO or CO diet resulted in extremely high blood levels of CSA. All levels were well above values known to be associated with marked renal dysfunction in man and animals. Thus, it appears unlikely that differences in renal dysfunction can be explained on a pharmocokinetic basis. The combined data support the concept that FO does not alter the bioavailability of CSA and therefore that such alteration does not account for the absence of CSA induced renal toxicity.

Macrophages have been implicated as the source of enhanced TxB$_2$ in murine lupus nephritis (Jackson, et al., *Kidney International* 31:460 (1987)). Since CSA induces an increase in mononuclear cells in the renal interstitium, macrophages could be responsible at least in part for an excess renal TxB$_2$ production. FO rich in omega-3 fatty acids reduces TxB$_2$ levels. This reduction is related to the high affinity of omega-3 fatty acids for cyclooxygenase and their inability to be used efficiently as substrate for dienoic metabolites. Thus, functional competitive inhibition limits the induction of CSA-induced TxB$_2$ production and maintains the hemodynamic balance essential for normal renal function. Improved renal function following inhibition of CSA-induced TxB$_2$ synthesis has been recently reported by Perico et al., *Am. J. Physiol.* 251:F581 (1986). Administration of the Tx synthetase inhibitor UK-38,485 to rats treated with CSA resulted in urinary TxB$_2$ levels comparable to control levels, as well as improved glomerular filtration rate (GFR). Total inhibition of Tx, however, did not return GFR to control levels, suggesting that other mediators participate in the loss of renal function induced by CSA.

In accordance with the above example, then, another embodiment of the instant invention provides a method of mediating the nephrotoxic effect of cyclosporine, comprising administering a diet comprising a fatty acid component. In yet another embodiment, there is provided a method of suppressing CSA-induced TxB$_2$ increase comprising administering a diet comprising a fatty acid component. In still a further embodiment, there is provided a method of suppressing CSA-induced decreases in prostaglandin, comprising administering a diet comprising a fatty acid component. The fatty acid component can be natural or synthetic, and in a preferred embodiment, may be derived from natural fish oil.

Having now fully described the present invention, it will be appreciated by those of skill in the art that the same can be performed within a wide and equivalent range of compositions, parameters, conditions and the like, without affecting the spirit or scope of the invention or of any embodiment therein.

What is claimed as new and intended to be covered by Letters Patent of the United States is:

1. A composition comprising a therapeutically effective amount of cyclosporine in combination with a fatty acid component, said fatty acid component comprising a fatty acid of the omega-3 family, or a pharmacologically acceptable salt thereof, wherein said fatty acid component is present in an amount effective to mediate the nephrotoxic effects of said cyclosporine.

2. The composition of claim 1, wherein said fatty acid component comprises eicosapentaenoic acid.

3. The composition of claim 1, wherein said fatty acid component comprises docosahexanoic acid.

4. The composition of claim 1, wherein said fatty acid component is synthetically produced.

5. The composition of claim 1 wherein said fatty acid component is derived from a natural source.

6. The composition of claim 1 wherein said fatty acid component comprises fish oil.

7. A method for mediating the nephrotoxic effect of cyclosporine in a host in need thereof comprising administering a therapeutically effective amount of said cyclosporine in combination with a fatty acid component, said fatty acid component comprising a fatty acid of the omega-3 family or a pharmacologically acceptable salt thereof, in an amount sufficient to mediate the nephrotoxic effects of said cyclosporine.

8. The method of claim 7, wherein said fatty acid component comprises eisosapentaenoic acid.

9. The method of claim 7, wherein said fatty acid component comprises docosahexanoic acid.

10. The method of claim 7, wherein said fatty acid component comprises fish oil.

11. The method of claim 7, wherein said fatty acid component is synthetically produced.

12. The method of claim 7, wherein said fatty acid component is derived from a natural source.

13. A method of reducing the synthesis of cyclosporine-induced renal prostaglandins in a host in need thereof comprising administering a therapeutically effective amount of said cyclosporine in combination with a fatty acid component, said fatty acid component comprising a fatty acid of the omega-3 family, or a pharmacologically acceptable salt thereof, in an amount effective to reduce renal prostaglandins.

14. The method of claim 13, wherein said fatty acid component comprises eicosapentaenoic acid.

15. The method of claim 13, wherein said fatty acid component comprises docosahexanoic acid.

16. The method of claim 13, wherein said fatty acid component comprises fish oil.

17. The method of claim 13, wherein said fatty acid component is synthetically produced.

18. The method of claim 13, wherein said fatty acid component is derived from a natural source.

19. A method of mediating the nephrotoxic effect of cyclosporine in a host in need thereof, said method comprising administering a therapeutically effective amount of said cyclosporine in combination with a diet comprising a fatty acid component, said fatty acid component comprising a fatty acid of the omega-3 family or a pharmacologically acceptable salt thereof, in an amount sufficient to mediate the nephrotoxic effects of said cyclosporine.

20. A method of suppressing cyclosporine-induced thromboxane increase in a host in need thereof, said method comprising administering a therapeutically effective amount of said cyclosporine in combination with a diet comprising a fatty acid component, said fatty acid component comprising a fatty acid of the omega-3 family or a pharmacologically acceptable salt thereof, in an amount sufficient to mediate the nephrotoxic effects of said cyclosporine.

21. A method of suppressing cyclosporine-induced prostaglandin decrease in a host in need thereof, said method comprising administering a therapeutically effective amount of said cyclosporine in combination with a diet comprising a fatty acid component, said fatty acid component comprising a fatty acid of the omega-3 family or a pharmacologically acceptable salt thereof, in an amount sufficient to mediate the nephrotoxic effects of said cyclosporine.

* * * * *